United States Patent [19]

Meyer et al.

[11] 4,172,045

[45] Oct. 23, 1979

[54] PROCESS FOR THE MANUFACTURE OF 2-STILBENYL-1,2,3-TRIAZOLES WHICH CONTAIN CARBOXYL GROUPS, NOVEL 2-STILBENYL-1,2,3-TRIAZOLES WHICH CONTAIN CARBOXYL GROUPS AND THE USE THEREOF AS FLUORESCENT BRIGHTENERS

[75] Inventors: Hans R. Meyer, Binningen; Reinhard Zweidler, Basel, both of Switzerland

[73] Assignee: Ciba-Geigy Corporation, Ardsley, N.Y.

[21] Appl. No.: 751,221

[22] Filed: Dec. 16, 1976

Related U.S. Application Data

[63] Continuation of Ser. No. 609,274, Sep. 2, 1975, abandoned.

[30] Foreign Application Priority Data

Sep. 9, 1974 [CH] Switzerland .................. 12225/74

[51] Int. Cl.$^2$ .................. C07D 249/20; C07D 249/24
[52] U.S. Cl. .................. 252/301.22; 542/462; 542/463; 427/158; 8/1 W
[58] Field of Search .................. 542/462, 463; 252/301.22; 8/1 W

[56] References Cited

U.S. PATENT DOCUMENTS 3,781,278  12/1973  Siegrist et al. .................. 542/462 X

FOREIGN PATENT DOCUMENTS

| | | | |
|---|---|---|---|
| 162426 | 4/1955 | Australia .................. | 542/463 |
| 2010764 | 10/1970 | Fed. Rep. of Germany .................. | 542/463 |
| 41-13148 | 7/1966 | Japan .................. | 542/463 |
| 1113539 | 5/1968 | United Kingdom .................. | 542/463 |
| 1271052 | 7/1970 | United Kingdom . | |

*Primary Examiner*—Arthur P. Demers
*Attorney, Agent, or Firm*—Prabodh I. Almaula

[57] ABSTRACT

Process for the manufacture of 2-stilbenyl-1,2,3-triazoles containing carboxyl groups by reacting a 2-tolyl-1,2,3-triazole with an anil in the presence of a strongly basic alkali compound in a strongly polar, neutral to basic organic solvent as well as novel 2-stilbenyl-1,2,3-triazoles containing carboxyl groups are described.

12 Claims, No Drawings

PROCESS FOR THE MANUFACTURE OF 2-STILBENYL-1,2,3-TRIAZOLES WHICH CONTAIN CARBOXYL GROUPS, NOVEL 2-STILBENYL-1,2,3-TRIAZOLES WHICH CONTAIN CARBOXYL GROUPS AND THE USE THEREOF AS FLUORESCENT BRIGHTENERS

This is a continuation of application Ser. No. 609,274, filed on Sept. 2, 1975, now abandoned.

The present invention provides a process for the manufacture of 2-stilbenyl-1,2,3-triazoles which contain carboxyl groups, novel 2-stilbenyl-1,2,3-triazoles which contain carboxyl groups and a process for optically brightening synthetic organic material which comprises the use of these novel compounds.

A number of different processes for the manufacture of stilbene compounds are known. One such process of wide application has become known as the "anil synthesis" (cf. for example Helvetica Chemica Acta 50, (1967) 906 ff, 55 (1972) 818–851 and 2300–2329 and 57, (1974) 81 ff.). As condition for the course of the anil synthesis, however, the absence of salt-forming substituents, e.g. of the carboxylic acid group, in the reactants has so far been given (cf. Helvetica Chimica Acta 50, (1967) 912 and 52, (1969) 2524).

Surprisingly, it has now been found that 2-stilbenyl-1,2,3-triazoles which contain carboxyl groups can be manufactured in good yield by means of the anil synthesis. This process makes it possible to manufacture commercially important compounds in a particularly advantageous manner. A substantial number of new compounds, as well as of known ones which it has hitherto only been possible to obtain in part by roundabout methods, can now be manufactured in simple manner and in improved yield.

The classic process for manufacturing 2-stilbenyl-naphthotriazoles consists in starting from 4-nitrostilbene derivatives of the formula (A), reducing these to the 4-aminostilbenes which are then diazotised, coupled with 2-naphthylamines and then oxidized. It is known that 4-nitrostilbene derivatives are only obtained from p-nitrotoluene derivatives in accordance with the following reaction equation in satisfactory yield if X represents an electronegative radical, e.g. —NO₂, —CN, —SO₂Ophenyl, SO₃H, —COOH, —CON(alkyl)₂ or —SO₂N(alkyl)₂:

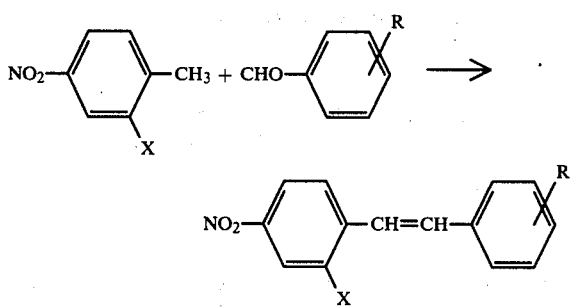

However, this reaction takes place with poor yield or even fails if X represents hydrogen or other non-electronegative substituents.

The present invention accordingly provides a process for the manufacture of 2-stilbenyl-1,2,3-triazoles of the formula

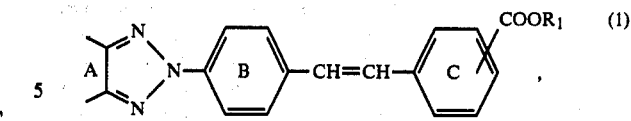

wherein A represents a benzene or naphthalene ring which is unsubstituted or substituted by non-chromophoric groups and $R_1$ represents hydrogen or a salt-forming cation and the benzene nuclei B and C are unsubstituted or substituted by non-chromophoric groups, which process comprises reacting a 2-tolyl-1,2,3-triazole of the formula

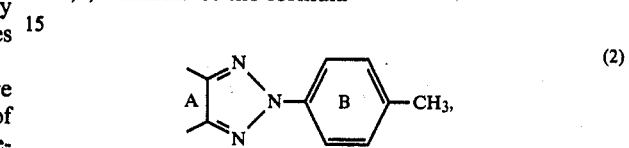

wherein A is as defined above, with an anil of the formula

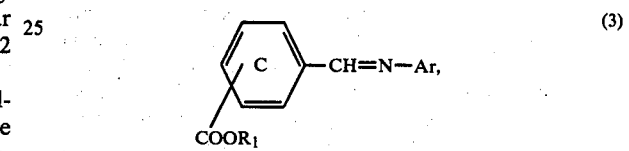

wherein $R_1$ is as defined above and Ar represents an unsubstituted or a substituted aromatic radical, in the presence of a strongly basic alkali compound in a strongly polar, neutral to basic organic solvent or mixtures thereof.

Examples of suitable non-chromophoric substituents in the nucleus A are alkyl, fluorine, bromine, chlorine, alkoxy, alkoxyalkoxy, aryloxy, aralkoxy, aryloxyalkoxy, alkenyloxy, aryl, alkylmercapto, alkenylmercapto, arylmercapto, arylsulphonyl, cyano, carboxy, carbalkoxy, carbamoyl and suphonyl. Two substituents in the ortho-position can also together form an alkylene radical with 5 to 6 ring members which can be optionally interrupted by heteroatoms, e.g. methylenedioxy. Preferred substituents are in general alkyl of 1 to 4 carbon atoms, alkoxyalkyl of 2 to 5 carbon atoms, phenyl, chlorine, alkoxy of 1 to 4 carbon atoms, benzyloxy, phenoxy, alkylmercapto of 1 to 4 carbon atoms, alkenyloxy of 3 to 4 carbon atoms, phenylmercapto, carboxy, carbamoyl and sulphonyl.

Preferred carbamoyl and sulphamoyl radicals can be represented by the formulae

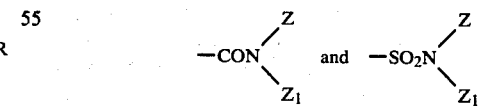

respectively, wherein each of Z and $Z_1$ independently represents hydrogen, preferably alkyl of 1 to 4 carbon atoms, or together with the nitrogen atom they represent the completion of a non-aromatic ring with 5 to 7 members, e.g. a morpholino or piperidino ring.

The term "carboxy" is to be understood as meaning herein the radical —COOM, wherein M represents hydrogen or a salt-forming cation. Possible salt-forming cations M are in general those of alkaline earth metals, e.g. calcium, barium or magnesium, as well as of alkali metals, e.g. sodium or potassium, and also ammonium which is substituted by alkyl or hydroxyalkyl of 1 to 4 carbon atoms or is unsubstituted, or amine salts of cyclic amines, e.g. pyridine, morpholine or piperidine. Besides hydrogen, M preferably represents in particular the potassium and the sodium cation.

The aromatic radical Ar is made up as a rule from one or more 6-membered carbocycles; preferably it represents a substituted or an unsubstituted naphthalene radical and especially a chlorine-substituted or an unsubstituted phenyl radical.

An interesting process for the manufacture of 2-stilbenyl-1,2,3-triazoles of the formula

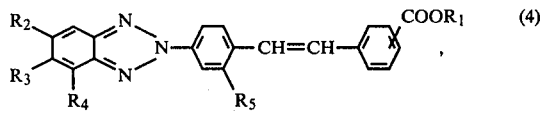 (4)

wherein $R_1$ represents hydrogen or a salt-forming cation, $R_2$ represents hydrogen, alkoxy of 1 to 4 carbon atoms, carboxyalkoxy of 2 to 6 carbon atoms or together with $R_3$ represents methylenedioxy, $R_3$ represents hydrogen, alkoxy of 1 to 4 carbon atoms, carboxyalkoxy of 2 to 6 carbon atoms, alkoxyalkoxy of 2 to 6 carbon atoms, phenoxy, phenoxyalkyl of 1 to 3 carbon atoms in the alkyl moiety, chlorine, alkylmercapto, phenylmercapto, alkyl of 2 to 4 carbon atoms, or together with $R_2$ represents methylenedioxy or together with $R_4$ represents the completion of an unsubstituted naphthalene ring or of a naphthalene ring which is substituted by chlorine, alkoxy of 1 to 4 carbon atoms or

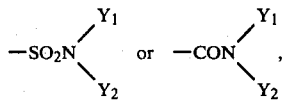

in which each of $Y_1$ and $Y_2$ independently represents alkyl of 1 to 4 carbon atoms or together with the nitrogen atom they represent the completion of a non-aromatic ring with 5 to 7 members, $R_4$ represents hydrogen or together with $R_3$ represents the completion of an unsubstituted naphthalene ring or of a naphthalene ring which is substituted by chlorine, alkoxy of 1 to 4 carbon atoms or

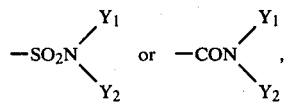

in which each of $Y_1$ $Y_2$ independently represents alkyl of 1 to 4 carbon atoms or together with the nitrogen atom they represent the completion of a non-aromatic ring with 5 to 7 members, $R_5$ represents hydrogen, chlorine, alkoxy of 1 to 4 carbon atoms, preferably methoxy,

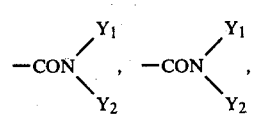

in which $Y_1$ and $Y_2$ have the meanings already assigned to them, or represents —SO$_2$-phenyl, is that which comprises reacting a 2-tolyl-1,2,3-triazole of the formula

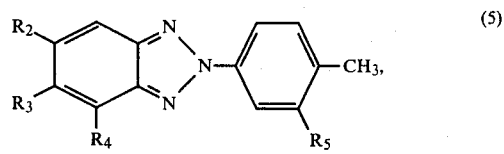 (5)

wherein $R_2$, $R_3$, $R_4$ and $R_5$ have the indicated meanings, with an anil of the formula

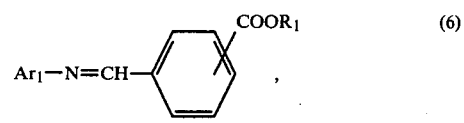 (6)

wherein $Ar_1$ represents an unsubstituted or a substituted naphthalene radical or preferably a chlorine-substituted or an unsubstituted phenyl radical and $R_1$ has the indicated meaning.

A preferred process for the manufacture of 2-stilbenyl-1,2,3-triazoles of the formula

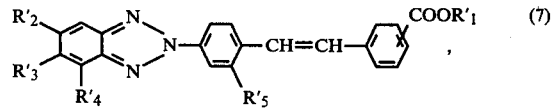 (7)

werein $R_1'$ represents a hydrogen, alkali metal, alkaline earth metal, ammonium or amine salt ion, $R_2'$ represents hydrogen, alkoxy of 1 to 4 carbon atoms or together with $R_3'$ represents methylenedioxy, $R_3'$ represents hydrogen, alkoxy of 1 to 4 carbon atoms, phenoxy, phenoxyalkoxy of 1 to 3 carbon atoms in the alkoxy moiety, chlorine, or together with $R_2'$ represents methylenedioxy or together with $R_4'$ represents the completion of an unsubstituted naphthalene ring or of a naphthalene ring which is substituted by alkoxy of 1 to 4 carbon atoms, $R_4'$ represents hydrogen or together with $R_3'$ represents the completion of an unsubstituted naphthalene ring or of a naphthalene ring which is substituted by alkoxy of 1 to 4 carbon atoms, and $R_5'$ represents hydrogen, —CONY$_1$Y$_2$, wherein each of $Y_1$ and $Y_2$ independently represents alkyl of 1 to 4 carbon atoms or together with the nitrogen atom represent the completion of a non-aromatic ring with 5 to 7 members, is that which comprises reacting a 2-tolyl-1,2,3-triazole of the formula

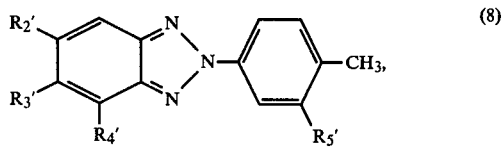 (8)

wherein $R_2'$ to $R_5'$ have the meanings assigned to them hereinbefore, with an anil of the formula

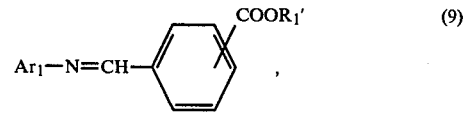 (9)

wherein Ar₁ represents unsubstituted or substituted phenyl or naphthyl and R₁' has the meaning assigned to it represents An especially preferred process for the manufacture of 2-stilbenyl-npahtho-1,2,3-triazoles of the formulae

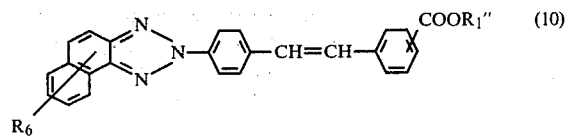

and

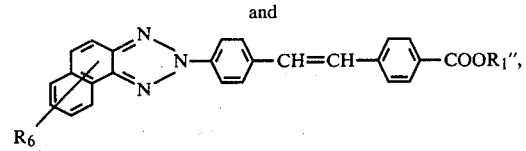

wherein R₁'' represents a hydrogen, alkali metal, ammonium or amine salt ion, and R₆ represents hydrogen or alkoxy of 1 to 4 carbon atoms, is that which comprises reacting a 2-tolyl-naphtho-1,2,3-triazole of the formula

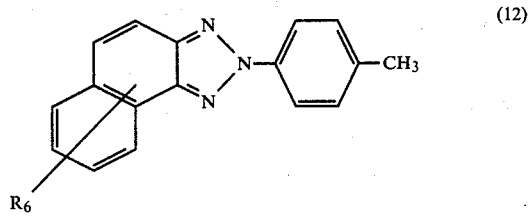

wherein R₆ has the indicated meaning, with an anil of the formula

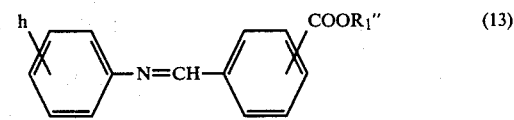

or

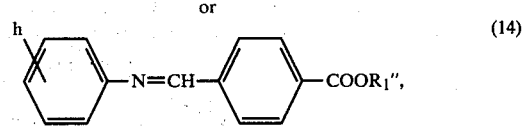

wherein h represents chlorine or hydrogen and R₁'' has the meaning previously assigned to it. The process for the manufacture of compounds of the formulae (10) and (11), wherein R₆ is hydrogen, is particularly preferred.

Also deserving of mention is the process for the manufacture of 2-stilbenyl-benzo-1,2,3-triazoles of the formula

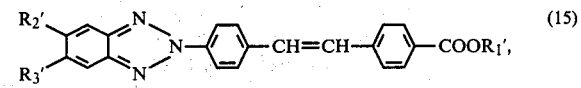

wherein R₁', R₂' and R₃' have the meanings previously assigned to them, which process comprises reacting a 2-tolyl-benzo-1,2,3-triazole of the formula

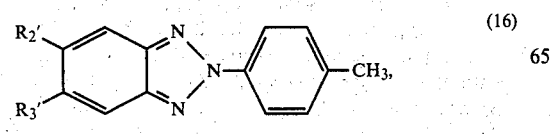

wherein R₂' and R₃' have the meanings assigned to them hereinbefore, with an anil of the formula

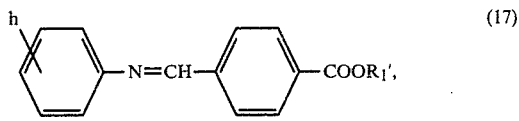

wherein h and R₁' have the meanings assigned to them hereinbefore.

The reaction products of the formulae (1), (4), (7), (10), (11) and (15) can, if appropriate, be esterified. The esterification is carried out in a manner known per se by reacting the acid with an alkanol, alkenol, phenol, hydroxyalkylbenzene or cycloalkanol, as e.g. methanol, ethanol, n-propanol, isopropanol, n-butanol, sec. butanol, isobutanol, tert. butanol, n-hexanol, n-octanol, 2-ethylhexanol, ethylene chlorohydrin, propylene chlorohydrin, 3-chloro-1-propanol, ethylene glycol monomethyl ether, ethylene glycol monoethyl ether, ethylene glycol monobutyl ether, ethylene glycol isopropyl ether, 1-methoxy-2-propanol, butyl glycolate glycolic nitrile, 3-hydroxypropionitrile, ethyl lactate, allyl alcohol, crotyl alcohol, phenol, o-, m- and p-cresol, o-chlorophenyl, tert. butylphenol, benzyl alcohol, 2-phenoxyethanol, 1-phenylethanol, cyclopentanol and cyclohexanol. The esterification is effected, for example, in the presence of an acid catalyst, such as sulphuric acid, hydrogen chloride or p-toluenesulphonic acid, optionally with simultaneous removal of the water of reaction as an azeotrope with a suitable entrainer, as e.g. perchloroethylene, xylene, chlorobenzene or higher boiling petroleum ether fractions. However, it is also possible to manufacture the esters by way of the corresponding carboxylic chlorides by reacting the carboxylic acids first with thionyl chloride, phosphoroxy chloride etc. and heating the reaction products, with or without isolating them first, with the alcohols or phenols.

The process according to the invention also makes it possible to manufacture in good yield interesting compounds of the formula (1), wherein the benzene nucleus does not necessarily contain electronegative substituents.

Within to scope of compounds of formula (7) and of their esters the compounds of particular interest are (a) 2-stilbenzyl-1,2,3-triazoles of the formula

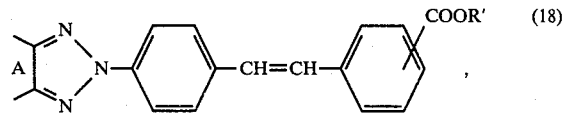

wherein A represents a benzene or naphthalene ring which is unsubstituted or substituted by non-chromophoric groups and R' represents alkyl of 1 to 4 carbon atoms, haloalkyl of 1 to 4 carbon atoms, alkoxyalkyl of 2 to 8 carbon atoms, cyanoalkyl of 1 to 4 carbon atoms, alkenyl of 3 or 4 carbon atoms or phenoxyalkyl of 1 to 3 carbon atoms in the alkyl moiety and in case A represents a benzene ring substituted by non-chromophoric groups R' also represents hydrogen or a salt forming-cation, (b) 2-stilbenyl-1,2,3-triazoles of the formula

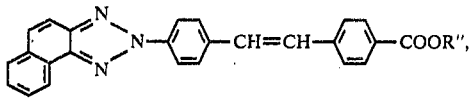

(19)

wherein R" represents alkyl of 2 to 4 carbon atoms, and (c) the compound of the formula

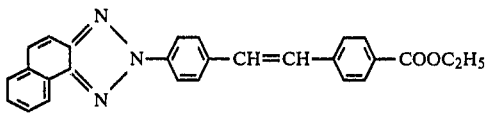

(20)

and for the optically brightening of polyesters in the spinning melt the compounds of the formula

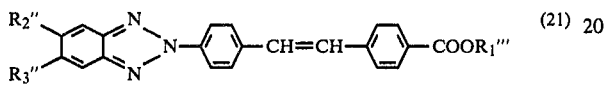

(21)

wherein
$R_1'''$ represents a hydrogen, alkalimetal, ammonium, amine salt ion or alkyl with 1 to 4 carbon atoms,
$R_2'$ represents hydrogen, alkoxy with 1 to 4 carbon atoms or together with $R_3''$ represents methylenedioxy and
$R_3''$ represents alkoxy with 1 to 4 carbon atoms or together with $R_2''$ represents methylenedioxy, and particularly those compounds of the formula

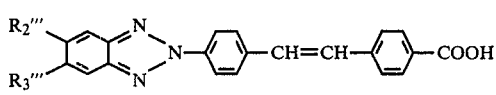

(22)

wherein
$R_2'''$ represents hydrogen or alkoxy with 1 to 4 carbon atoms, particularly methoxy and
$R_3'''$ represents alkoxy with 1 to 4 carbon atoms, particularly methoxy.

2-Stilbenyl-1,2,3-triazoles of the formulae (18), (19) and (21) wherein R', R" and R''' are different from hydrogen or a salt-forming cation can be manufactured by esterification in known manner of the corresponding carboxylic acid with an alcohol, for example ethanol, n-propanol, isopropanol, n-butanol, sec. butanol, isobutanol, tert. butanol, ethylene chlorohydrin, propylene chlorohydrin, 3-chloro-1-propanol, ethylene glycol monomethyl and monoethyl ether, ethylene glycol monobutyl ether, ethylene glycol isopropyl ether, allyl alcohol, crotyl alcohol, 2-phenoxyethanol, 3-phenoxypropanol, 1-phenylethanol, cyclopentanol and benzyl alcohol.

The starting materials, i.e. the compounds of the formulae (2), (3), (5), (6), (8), (9), (11) and (12), are known or can be manufactured in a manner which is known per se. The anils of the formulae (3), (6), (9) and (12) are therefore manufactured by reacting an aromatic amine or a substituted or unsubstituted naphthylamine or aniline or an unsubstituted or a chlorine-substituted aniline with, for example, o-carboxybenzaldehyde, m-carboxybenzaldehyde, p-carboxybenzaldehyde, 2-carboxy-5-methoxy-benzaldehyde, 2-methyl-4-carboxybenzaldehyde, 2-chloro-5-carboxybenzaldehyde. The manufacture of the 2-tolyl-naphthotriazoles is effected in accordance with Helv. Chim. Acta 55 (1972) 849 and that of the 2-tolyl-benzotriazoles in accordance with Helv. Chim. Acta 55 (1972) 2325.

The compounds containing methyl groups can be reacting with the anils in the presence of a suitable strongly polar, neutral to alkaline organic solvent or mixtures thereof which do not contain atoms, in particular hydrogen atoms, that can be replaced by alkali metals. In practice, suitable solvents of this kind are primarily dialkylated acylamides of the type $$[(alkyl)_2N]_w\text{—acyl} \qquad (23)$$

wherein "alkyl" represents a lower alkyl group of 1 to 4 carbon atoms, in particular a methyl group, "acyl" represents the radical of a lower carboxylic acid of 1 to 4 carbon atoms, in particular formic or phosphoric acid, and w indicates the basicity of the acid. As important examples of such solvents there may be mentioned: diethyl formamide, dimethyl acetamide and especially dimethyl formamide and hexamethylphosphoric triamide. Suitable solvents are also N-alkyl-lactames of 5 to 10 carbon atoms, e.g. N-methylpyrrolidone and tetraalkylureas, such as tetramethylurea.

As has been mentioned already, a strongly basic alkali compound is also necessary for carrying out the reaction. Suitable for this purpose, depending on the nature of the solvent and the reactivity of the anil, are alkali metal alcoholates or hydroxides, in particular postassium and sodium compounds of the composition $$KOC_{m-1}H_{2m-1} \text{ and } NaOC_mH_{2m+1} \qquad (24),$$

respectively, wherein m is an integer from 1 to 6, for example potassium hydroxide, potassium tert. butylate, sodium tert. butylate or sodium methylate. When using such alkali alcoholates the process must be carried out in virtually anhydrous medium, whereas a small water content of up to app. 15% is permissable when using potassium hydroxide. It is advantageous to use potassium hydroxide and sodium methylate e.g. in combination with hexamethylphosphoric triamide at elevated temperature, e.g. at 110°-130° C. It is of course also possible to use mixtures of such bases. The use of potassium tert. butylate is preferred.

The compounds containing methyl groups are desirably reacted with the anils in equivalent amounts, so that there is no substantial excess of either component, although on occasion an excess of anil of up to app. 50% can often be of advantage. It is advantageous to use at least the equivalent amount of alkali compound, i.e. at least 1 mole of a compound with e.g. one KO group to 1 mole of aldehyde anil. When using potassium hydroxide, it is preferable to do so in 4 to 8 times the equivalent amount. Particularly good yields are obtained on using potassium tert. butylate in one to six times, preferably two to four times, the equivalent amount.

The reaction according to the invention can usually be carried out at temperatures in the range between about 10° and 150° C. When using particularly reactive anils and and particularly energetic catalysts, e.g. potassium tert. butylate, the reaction takes place frequently even at room temperature, in which case it is not necessary to apply heat externally. This is especially advantageous if the reactants contain ring compounds or substituents which can be easily opened or split off by alkali or which can be chemically changed in some other way. This applies, for example, to anils which contain chlorine substituents which can be easily split off. However, it most advantageous to carry out the process at elevated temperature, especially when using sodium alcoholates and potassium hydroxide. For example, the reaction mixture is heated slowly to 30° to 90° C. and then kept at this temperature for a time, e.g. from ½ to 2 hours.

The manufacture of the anil and the reaction thereof with the tolyl compound can also be carried out consecutively in the one reaction vessel. For example, the aldehyde is heated with excess aniline in dimethyl formamide and the reaction mixture is completely evaporated to dryness in vacuo. A tolyl component and dimethyl formamide are added and the usual procedure is carried out.

The final products can be worked up from the reaction mixture by conventional methods which are known per se. The isolation of the carboxylic acids in salt form is effected for example by precipitation with water, while the free carboxylic acids can be precipitated by acidification with a strong mineral acid, as for example aqueous hydrochloric acid. The compounds of the formulae (1), (4), (7), (10), (11) and (15) and the esters thereof are mostly useful fluorescent brighteners. They can be used in known manner for brightening organic materials of high molecular weight of the most widely different kind, preferably synthetic organic materials, in which connection the free carboxylic acids and the esters thereof are used with advantage for polyester and the carboxylic acid salts for polyamide and polyacrylonitrile.

The carboxylic acid esters are particularly suitable for brightening polyester materials by the high temperature exhaustion process.

Without any restriction being implied by the following classification, examples of organic materials are:

I. Synthetic organic materials or high molecular weight:

(a) polymerisation products based on organic compounds containing at least one polymerisable carbon-carbon double bond, that is to say their homopolymers or copolymers as well as their aftertreatment products, for example, crosslinking, grafting or degradation products, polymer blends, or products obtained by modification of reactive groups, for example polymers based on α,β-unsaturated carboxylic acids or derivatives of such carboxylic acids, especially on acrylic compound for example acrylic esters, acrylic acid, acrylonitrile, acrylic amides and their derivatives or their methacryl analogues), on olefin hydrocarbons (for example ethylene, propylene, styrenes or dienes and also ABS polymers), and polymers based on vinyl and vinylidene compounds (for example vinyl chloride, vinyl alcohol and vinylidene chloride);

(b) polymerisation products which can be obtained by ring opening, for example, polyamides of the polycaprolactam type, and also polymers which are obtained both by polyaddition and by polycondensation, for example polyethers or polyacetals, (c) polycondensation products or precondensates based on bifunctional or polyfunctional compounds with condensable groups, their homocondensation and co-condensation products, and aftertreatment products, for example polyesters, especially saturated (for example ethylene glycol terephthalic acid polyester) or unsaturated (for example maleic acid-dialcohol polycondensates as well as their crosslinking products with copolymerisable vinyl monomers), unbranched and branched (also including those based on polyhydric alcohols, for example alkyd resins) polyesters, polyamides (for example hexamethylenediamine adipate), maleic resins, melamine resins, their precondensates and analogues, polycarbonates and silicones;

(d) polyaddition products, such as polyurethanes (crosslinked and non-crosslinked) and epoxide resins.

II. Regenerated man-made organic materials, for example, cellulose esters of varying degrees of esterification (so-called 2½ acetate or triacetate) or cellulose ethers, regenerated cellulose (viscose or cuprammonium cellulose), or their aftertreatment products, and casein plastics.

III. Natural organic materials of animal or vegetable origin, for example based on cellulose or proteins, such as cotton, wool, linen, silk, varnish gums, starch and caseins.

The organic materials to be optically brightened can be in the most diverse states of processing (raw materials, semi-finished goods or finished goods). On the other hand, they can be in the form of structures of the most diverse shapes, for example predominantly three-dimensional structures such as sheets, profiles, injection mouldings, various machined articles, chips, granules or foams, and also predominantly two-dimensional structures, such as films, foils lacquers, coatings and impregnations, or predominantly one-dimensional bodies, such as filaments, fibres, flocks and wires. The said materials can, on the other hand, also be in an unshaped state, in the most diverse homogeneous or inhomogeneous forms of division, as for example, in the form of powders, solutions, emulsions, dispersions, latices, pastes or waxes.

Fibre materials can, for example, be in the form of endless filaments (stretched or unstretched), staple fibres, flocks, hanks, textile filament yarns, threads, non-wovens, felts, waddings, flocked structures or woven textile or bonded textile fabrics, knitted fabrics and papers, cardboards or paper pulps.

The compounds to be used according to the invention are of importance, inter alia, for the treatment of organic textile materials, especially woven textile fabrics. If fibres which can be in the form of staple fibres or endless filaments or in the form of hanks, woven fabrics, knitted fabrics, fleeces, flocked substrates or bonded fabrics, are to be optically brightened according to the invention, this is advantageously effected in an aqueous medium, wherein the compounds in question are present in a finely divided form (suspensions, so-called microdispersions, or optionally solutions). If desired, dispersing agents, stabilisers, wetting agents and further assistants can be added during the treatment.

Depending on the type of brightener compound used, it can be advantageous to carry out the treatment in a neutral or alkaline or acid bath. The treatment is usually carried out at temperatures of 20° to 140° C., for example at the boiling point of the bath or near it (about 90° C.). Solutions or emulsions in organic solvents can also be used for the finishing according to the invention of textile substrates, as is practised in the dyeing industry in so-called solvent dyeing (pad-heating fixing application, or exhaustion dyeing processes in dyeing machines).

The new fluorescent brighteners according to the present invention can further be added to, or incorporated in, the materials before or during their shaping. Thus they can for example be added to the compression moulding composition or injection moulding composition during the manufacture of films, sheets (for example working into polyvinyl chloride in a single roller mill) or mouldings.

If the fashioning of man-made synthetic or regenerated man-made organic materials is effected by spinning processes or from spinning solutions/melts, the fluorescent brighteners can be applied by the following processes:

addition to the starting substances (for example monomers) or intermediates (for example precondensates or prepolymers), that is to say before or during the polymerisation, polycondensation or polyaddition, sprinkling in powder form on polymer chips or granules for spinning solutions/melts, bath dyeing of polymer chips or granules for spinning solutions/melt, metered addition to spinning melts or spinning solutions, and application to the spun tow before stretching.

The fluorescent brighteners according to the present invention can, for example, also be employed in the following use forms:

(a) in mixtures with dyestuffs (shading) or pigments (coloured pigments or especially, for example, white pigments), or as an additive to dye baths, printing pastes, discharge pastes or reserve pastes, or for the aftertreatment of dyeings, prints or discharge prints;

(b) in mixtures with carriers, wetting agents, plasticisers, swelling agents, anti-oxidants, ultraviolet absorbers, heat stabilisers and chemical bleaching agents (chlorite bleach or bleaching bath additives);

(c) in admixture with crosslinking agents or finishing agents (for example starch or synthetic finishes), and in combination with the most diverse textile finishing processes, especially synthetic resin finishes (for example creaseproof finishes such as wash-and-wear, permanent-press or non-iron), as well as flameproof finishes, soft handle finishes, anti-soiling finishes or anti-static finishes, or antimicrobial finishes;

(d) incorporation of the fluorescent brighteners into polymeric carriers (polymerisation, polycondensation or polyaddition products, in a dissolved or dispersed form, for use, for example, in coating agents, impregnating agents or binders (solutions, dispersions and emulsions) for textiles, non-wovens, papers and leather;

(e) as additives to master batches;

(f) as additives to the most diverse industrial products in order to render these more marketable (for example improving the appearance of soaps, detergents, pigments);

(g) in combination with other optically brightening substances;

(h) in spinning bath preparations, that is to say as additives to spinning baths which are used for improving the slip for the further processing of synthetic fibres, or from a special bath before the stretching of the fibre;

(i) as scintillators for various purposes of a photographic nature, for example, for electrophotographic reproduction, for the optical brightening of photographic layers, optionally in combination with white pigments, for example $TiO_2$.

(j) depending on the substitution as laser dyes.

If the brightening process is combined with textile treatment or finishing methods, the combined treatment can in many cases advantageously be carried out with the aid of appropriate stable preparations which contain the fluorescent brightener compounds in such a concentration that the desired brightening effect is achieved.

In certain cases, the fluorescent brighteners are made fully effective by an after-treatment. This can be, for example, a chemical treatment (for example acid treatment), a thermal treatment (for example heat) or a combined chemical/thermal treatment. Thus, for example, the appropriate procedure to follow in brightening a number of fibre substrates, for example polyester fibres, with the fluorescent brighteners according to the invention, is to impregnate these fibres with the aqueous dispersions (or optionally also solutions) of the brighteners at temperatures below 75° C., for example at room temperature, and to subject them to a dry heat treatment at temperatures above 100° C., it being generally advisable additionally to dry the fibre material beforehand at a moderately elevated temperature, for example at not less than 60° C. and up to about 130° C. The heat treatment in the dry state is then advantageously carried out at temperature between 120° and 225° C., for example by heating in a drying chamber, by ironing within the specified temperature range or by treatment with dry, superheated steam. The drying and dry heat treatment can also be carried out in immediate succession or be combined in a single process stage.

The amount of fluorescent brightener manufactured according to the invention to be used, referred to the weight of the material to be brightened, can vary within wide limits. A marked and lasting effect can be obtained even with very insignificant amounts, in certain cases 0.0001 percent by weight. But it is also possible to use amounts of up to app. 0.8 percent by weight and, on occasion, up to app. 2 percent by weight. For most practical purposes, it is preferable to use amounts between 0.0005 and 0.5 percent by weight.

The following Examples illustrate the invention, the percentages being by weight unless otherwise stated. Melting and boiling points, unless otherwise indicated, are uncorrected and to some extent approximate.

EXAMPLE 1

With stirring and passage of nitrogen, 134.7 g of potassium tert. butylate are added in small amounts at 60° C. to a solution of 77.8 g of the compound of the formula

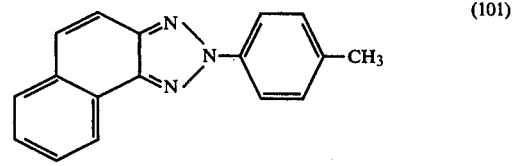

(101)

and 67.5 g of the anil of terephthal aldehyde acid in 1 liter of anhydrous dimethyl formamide, in the process of which the reaction mixture turns violet in colour. The temperature is allowed to rise to 80° C. and kept thereat for 1 hour. After the reaction mixture has been cooled in an ice bath, it is treated with 200 ml of water, acidified with 120 ml of conc. hydrochloric acid, and the precipitated product is filtered off with suction and washed repeatedly with water, methanol, acetone and chloroform. The filter product is dried in vacuo at 100° C. to yield 114.4 g (=97.4% of theory) of the carboxylic acid of the formula

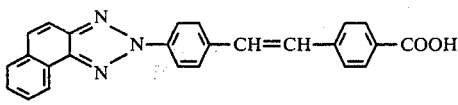 (102)

It is purified by recrystallization from dimethyl formamide and a small amount of water and then from diethylene glycol and by extraction with ethyl alcohol to give luminous, light yellow crystals which melt at 350° C. (with decomp.).

114.4 g of the crude carboxylic acid of the formula (102) are stirred under reflux in 31.9 ml of thionyl chloride and 1 liter of chlorobenzene until the evolution of hydrogen chloride has ceased and a solution is obtained (c. 1 hour). About 600 ml of solvent are distilled off and the residue is cooled. The precipitate is filtered off with suction and washed with 2×100 ml of chlorobenzene and dried, to yield 108.9 g (=91% of theory) of the acid chloride of the formula

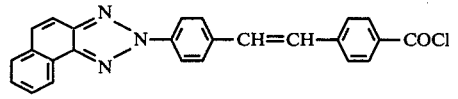 (103)

as light yellow crystals with a melting point of 224° C.

12.3 g of the compound of the formula (103) are dissolved under reflux in 90 ml of anhydrous chlorobenzene. With stirring, sufficient absolute alcohol is cautiously added dropwise to the hot solution to lower the reflux temperature to about 125° C., whereupon vigorous evolution of hydrogen chloride ensues. After refluxing for 1 hour, a further 80 ml of abs. alcohol are added and the batch is refluxed for a further hour with stirring. Filtration is effected at room temperature, the residue is washed with alcohol and dried at 100° C. in vacuum to yield the ethyl ester of the formula

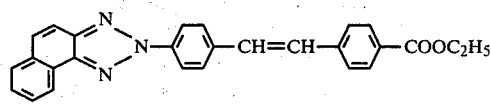 (104)

in the form of plae yellow crystals. Yield=c. 90% of theory; m.p. 171°–172° C. after recrystallisation from ethylene glycol monomethyl ether.

The carboxylic acids and their esters of the general formula (105) listed in Table I can be manufactured in similar manner.

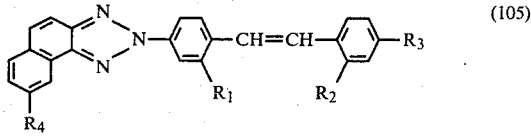 (105)

TABLE I

| No. | $R_1$ | $R_2$ | $R_3$ | $R_4$ | recrystallisation from: | m.p. °C. |
|---|---|---|---|---|---|---|
| 106 | —Cl | H | —COOH | H | TCB* | 350 |
| 107 | —CON(CH$_3$)(CH$_3$) | H | —COOH | H | DCB*, n-butanol | 272 |
| 108 | H | H | —COOH | —OCH$_3$ | TCB | 358 |
| 109 | H | —COOH | H | H | DCB | 251 |
| 110 | —Cl | H | —COO$_n$—C$_4$H$_9$ | H | n-butanol, toluene | 168 |
| 111 | —CON(CH$_3$)(CH$_3$) | H | —COOCH$_3$ | H | benzene, n-propanol | 198 |
| 112 | H | H | —COO$_n$—C$_4$H$_9$ | —OCH$_3$ | nonane, n-butanol | 152 |
| 113 | H | —COOCH$_3$ | H | H | nonane, n-butanol | 177 |

*TCB = 1,2,4-trichlorobenzene, DCB = o-dichlorobenzene

In the manufacture of the compound of the formula (102), it is also possible to use the p-chloroanil instead of the anil of terephthal aldehyde acid. The anil of terephthal aldehyde acid can also be replaced by its methyl or ethyl ester, when saponification occurs during the reaction.

EXAMPLE 2

With stirring and passage of nitrogen, 11.5 g of pulverised 88% potassium hydroxide are added at 60° C. to a solution of 7.8 g of the compound of the formula (101) and 6.75 of the anil of terephthal aldehyde acid in 180 ml of hexamethylphosphoric triamide. The temperature is raised slowly to 120° C. and kept thereat for 1 hour. After it has cooled, the dark blue reaction mixture is treated with 200 ml of water and acidified with 20 ml of concentrated hydrochloric acid. The precipitate is filtered off with suction, washed repeatedly with water, methanol, acetone and chloroform and dried in vacuo at 100° C. Yield: 11.1 g (=94.6% of theory) of the compound of the formula (102).

The compound of the formula (102) is also obtained by using sodium methylate instead of potassium hydroxide and otherwise carrying out the same procedure.

EXAMPLE 3

With stirring and passage of nitrogen, 11.5 g of sodium tert. butylate are added in small amounts at 50° C. to a solution of 7.8 g of the compound of the formula (101) and 6.75 g of the anil of terephthal aldehyde acid in 180 ml of anhydrous dimethyl formamide. The temperature is kept for ½ hour at 80° C. and then for 1 hour at 100° C. After the batch has been cooled in an ice bath, the dark reaction product is treated with 40 ml of water and acidified with 25 ml of conc. hydrochloric acid. The precipitate is filtered off with suction, washed repeatedly with water, methanol, acetone and chloroform and dried in vacuo at 100° C. Yield: 8.8 g of the compound of the formula (102).

The compound of the formula (102) is also obtained by using potassium tert. butylate instead of sodium tert. butylate and tetramethylurea, diethyl formamide or N-methylpyrrolidone as solvent, at a reaction temperature of 90° C.

EXAMPLE 4

8.1 g of 2-(p-tolyl)-5,6-dimethoxy-benztriazole are reacted with 6.75 g of the anil of terephthal aldehyde acid in accordance with Example 1. Yield: 11.3 g of the carboxylic acid of the formula

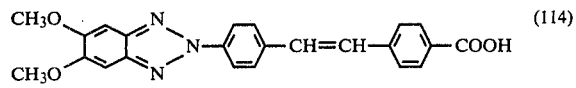

(114)

which is recrystallised from dimethyl formamide: m.p. 338° C.

Esterification with n-butanol yields the n-butyl ester of the formula

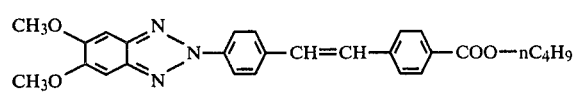

(115)

with a melting point of 170° C. after recrystallisation from petroleum ether (b.p. 170°–206° C.) and ethylene glycol monomethyl ether.

The compounds of the general formula

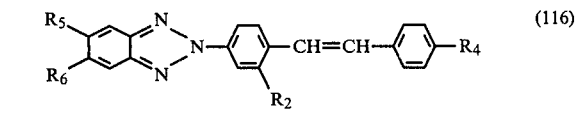

(116)

listed in Table II are obtained in corresponding manner. In the manufacture of the compound of the formula

TABLE II

| No. | $R_5$ | $R_6$ | $R_2$ | $R_4$ | m.p. °C. |
|---|---|---|---|---|---|
| (117) | OCH$_3$ | H | H | COOH | 317 |
| (118) | OCH$_3$ | H | H | COOC$_2$H$_5$ | 175 (approximate) |
| (119) | —O—CH$_2$—O— | | H | COOH | >350 |
| (120) | —O—CH$_2$—O— | | H | COOC$_4$H$_9$ | 222 |
| (121) | OCH$_3$ | —O—(CH$_2$)$_3$—O—C$_6$H$_5$ | Cl | COOH | 250 |
| (122) | OCH$_3$ | —O—(CH$_2$)$_3$—O—C$_6$H$_5$ | Cl | COOC$_2$H$_5$ | 195 |
| (123) | Cl | OCH$_3$ | H | COOH | >300 |

(123), the process is carried out at a temperature of 60° C. instead of 80° C.

EXAMPLE 5

Esterification of the carboxylic acid of the formula (102) with methanol, n-butanol, 3-phenoxypropanol, isopropanol, ethylene chlorohydrin, ethylene glycol monomethyl ether, allyl alcohol, phenol, 3-hydroxypropionitrile, cyclohexanol, n-propanol, isobutanol, sec. butanol, tert. butanol instead of with ethanol yields the esters of the general formula

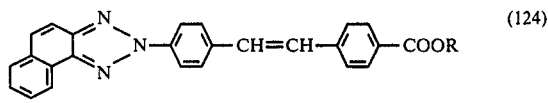

(124)

listed in Table III.

TABLE III

| Formula No. | R | m.p. °C. |
|---|---|---|
| (125) | —CH$_3$ | 227 |
| (126) | —C$_4$H$_9$ | 130 |
| (127) | —(CH$_2$)$_3$—O—C$_6$H$_5$ | 140 |
| (128) | —CH(CH$_3$)$_2$ | 166 |
| (129) | —CH$_2$CH$_2$Cl | 174 |
| (130) | —CH$_2$CH$_2$—OCH$_3$ | 150 |
| (131) | —CH$_2$—CH=CH$_2$ | 144 |
| (132) | —C$_6$H$_5$ | 200 |
| (133) | —CH$_2$CH$_2$CN | 183 |
| (134) | —C$_6$H$_{10}$H (cyclohexyl) | 172 |
| (135) | —CH$_2$CH$_2$CH$_3$ | 147 |
| (136) | —CH$_2$—CH(CH$_3$)$_2$ | 146 |
| (137) | —CH(CH$_3$)(C$_2$H$_5$) | 147 |
| (138) | —C(CH$_3$)$_3$ | 123 |

EXAMPLE 6

Using softened water, a bath is prepared which contains per liter 0.16% (referred to the weight of the fabric to be brightened) of the compound of the formula (104) (which has been predispersed with a small amount of water and app. 1 gram of a dispersant, e.g. an ethoxylated stearyl alcohol) and app. 2 g of a carrier. A suitable carrier is, for example, a mixture of dodecylbenzenesulphonate (as triethanolamine salt), ethoxylated ricinolic acid, n-hexanol and ethylene glycol in 1,2,4-trichlorobenzene.

A polyester fabric is put into this bath at 40° C. (liquor ratio 1:25). The bath is heated to 97° C. in the course of 30 minutes and held at this temperature for a further 30 minutes. After rinsing and drying it, a very strongly brightened polyester fabric is obtained.

EXAMPLE 7

Polyester fabric is treated in an autoclave in a bath of the following composition (liquor ratio 1:25):
0.16% (referred to the weight of the fabric to be brightened) of the compound of the formula (104) in finely dispersed form,
1.0 g of an ethoxylated stearyl alcohol,
1000 ml of softened water.

The bath is heated in the course of 30 minutes from 40° C. to 115° C. and held thereat for a further 30 minutes. The bath is then cooled and the fabric is rinsed and dried. A brilliant white polyester fabric is obtained.

Following the same procedure it is also possible to use the compounds of the formulae (126), (128), (135), (136), (137) or (138).

EXAMPLE 8

A polyester fabric (based on terephthalic acid/ethylene glycol) is padded at room temperature with an aqueous dispersion which contains per liter 2 g of one of the compounds of the formulae (104), (126), (128), (135), (136), (137) or (138) and 1 g of an adduct of about 8 moles of ethylene oxide and 1 mole of p-tert. octylphenol, and subsequently dried at app. 100° C. The treated material exhibits a strong white effect.

A strong white effect is also obtained by using instead of the above polyester fabric one that is obtained by condensation with 2 to 5 molar percent of isophthalic acid-5-sodium sulphonate (Dacron 64).

EXAMPLE 9

100 parts of terephthalic acid/ethylene glycol polyester granules are intimately mixed on each occasion The with 0.05 part of one of the compounds of the formulae (102), (104), (126), (128), (114), (115), (117) or (118) and melted, with stirring, at 285° C. The spinning melt is spun through conventional spinnerets to give strongly whitened polyester fibres.

EXAMPLE 10

A polyamide fabric (Perlon) is put at 60° C., in the liquor ratio of 1:40, into a bath which contains (referred to the weight of the fabric) 0.1% of one of the fluorescent brighteners of the formulae (102), (104), (126) or (128) and, per liter, 1 g of 80% acetic acid and 0.25 g of an adduct of 30 to 35 moles of ethylene oxide and 1 mole of commercial stearyl alcohol. The bath is heated within 30 minutes to boiling temperature and kept at the boil for 30 minutes. The fabric is then rinsed and dried. A strong white effect of good light fastness is obtained.

Similarly good white effects are obtained by using a fabric made of polyamide 66 (nylon) instead of polyamide 6.

Finally, it is also to carry out the process under high temperature conditions, e.g. over the course of 30 minutes at 130° C. For this kind of application it is advisable to add 3 g/l of hydrosulphite to the solution.

EXAMPLE 11

10,000 g of polyamide chips obtained in known manner from hexamethylenediamine adipate are mixed for 12 hours in a roller vessel with 30 g of titanium dioxide (rutile modification) and 5 g of one of the compounds of the formulae (102), (104), (126) or (128). The treated chips are melted in a boiler which is heated with oil or diphenyl vapour to 300°–310° C., after expulsion of the atmospheric oxygen with steam, and stirred for half an hour. The melt is then pressed out through a spinneret under a nitrogen pressure of 5 atmos. (gauge) and the spun, cooled filament is wound on a spool. The threads obtained exhibit a good white effect.

Similarly good results are obtained by using a polyamide obtained from ε-caprolactam instead of from hexamethylenediamine adipate.

EXAMPLE 12

A cellulose acetate fabric is put at 50° C. into an aqueous bath (liquor ratio 1:30 to 1:40) which contains 0.15% (based on the weight of the fabric) on one of the compounds of the formulae (104), (126) or (128). The temperature of the treatment bath is brought to 90°–95° C. and kept thereat for 30 to 45 minutes. After the fabric has been rinsed and dried, a good white effect is obtained.

EXAMPLE 13

An intimate mixture of 100 parts of polyvinyl chloride, 3 parts of a stabiliser (Advastat BD 100:Ba/Cd complex), 2 parts of titanium dioxide, 59 parts of dioctyl phthalate and 0.01 to 0.2 part of one of the compounds of the formulae (102), (104), (126) or (128), are rolled out to a sheet on a calender at 150° C. to 155° C.

The resultant opaque polyvinyl chloride sheet has a markedly higher white content than a sheet that does not contain the fluorescent brightener.

EXAMPLE 14

A casting compound that consists of polyacrylonitrile, 0,2 g of titanium dioxide (anatase modification) as matting agent, and 40 ml of dimethyl formamide, and which contain 5 mg of one of the compounds of the formulae (102), (104), (126) or (128), is poured onto a glass plate and drawn out with a metal rod to form a thin film. After it has dried, the film has a pronounced white effect.

EXAMPLE 15

A 27% polyurethane casting compound in ethyl acetate which contains, referred to the plastics dry weight, 2% of titanium dioxide (anatase modification), 5% of a stabiliser and 5% of a catalyst as well as 0.05% of the compound of the formula (104) or (126), is poured onto a glass plate and drawn out with a metal rod to form a thin film. After it has dried, the film has a pronounced white effect.

EXAMPLE 16

100 parts of polystyrene and 0.1 part of one of the compounds of the formulae (104), (126) or (128) are melted in a tube of 1 cm diameter for 20 minutes at 210° C. excluding air. After the melt has cooled, a brightened polystryene compound of good light fastness is obtained.

EXAMPLE 17

Polypropylene fibres are treated with 0.02 to 0.4% of the formula (104) for 60 minutes at 60° to 100° C. in a bath (liquor ratio 1:40) which contains per liter 5 g of an adduct of app. 35 moles of ethylene oxide and 1 mole of octadecyl alcohol, and 0.5 g of trisodium phosphate. The material is then rinsed and dried. The polypropylene fibres have a markedly higher white content than untreated fibres.

A similar effect is obtained by using 1 g of 85% formic acid instead of 0.5 g of trisodium phosphate.

We claim:

1. A 2-stilbenyl-1,2,3-triazole of the formula

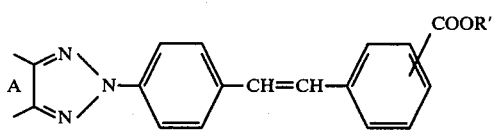

wherein A represents a benzene or naphthalene ring which is unsubstituted or substituted by non-chromophoric groups and R' represents alkyl of 2 to 4 carbon atoms, haloalkyl of 1 to 4 carbon atoms, alkoxyalkyl of 2 to 8 carbon atoms, cyanoalkyl of 1 to 4 carbon atoms, alkenyl of 3 or 4 carbon atoms, or phenoxyalkyl of 1 to 3 carbon atoms in the alkyl moiety, and in case A represents a benzene ring substituted by non-chromophoric groups selected from the group consisting of one or two alkoxy radicals with 1 to 4 carbon atoms, halogen or the methylenedioxy radical, R' also represents a hydrogen or salt-forming cation.

2. A 2-stilbenyl-1,2,3-triazole according to claim 1 of the formula

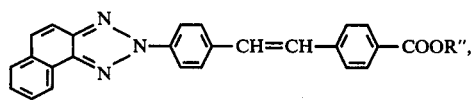

wherein R" represents alkyl of 2 to 4 carbon atoms.

3. A 2-stilbenyl-1,2,3-triazole according to claim 2 of the formula

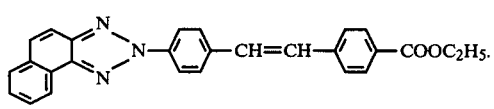

4. A 2-stilbenyl-1,2,3-triazole of the formula

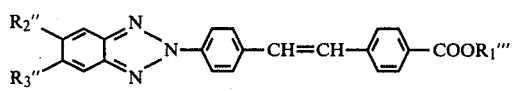

wherein $R_1'''$ represents a hydrogen, alkalimetal, ammonium, amine salt ion or alkyl with 1 to 4 carbon atoms, $R_2''$ represents hydrogen, alkoxy with 1 to 4 carbon atoms or together with $R_3''$ represents methylenedioxy and $R_3''$ represtns alkoxy with 1 to 4 carbon atoms or together with $R_2''$ represents methylenedioxy.

5. A 2-stilbenyl,1,2,3-triazole according to claim 4 of the formula

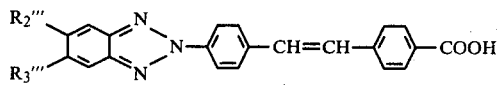

wherein $R_2'''$ represents hydrogen or alkoxy with 1 to 4 carbon atoms and $R_3'''$ represents alkoxy with 1 to 4 carbon atoms.

6. A stilbenyl-1,2,3-triazole according to claim 5 of the formula

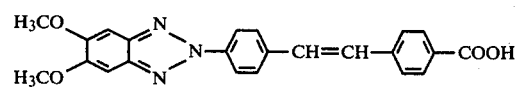

7. A 2-stilbenyl-1,2,3-triazole according to claim 5 of the formula

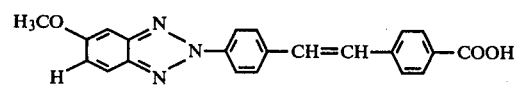

8. A process for optically brightening a synthetic organic material which comprises incorporating therein or applying thereto a 2-stilbenyl-1,2,3-triazole as defined in claim 1.

9. A process according to claim 8 for optically brightening polyesters which comprises incorporating in a polyester spinning melt a 2-stilbenyl-1,2,3-triazole as defined in claim 4.

10. A process according to claim 9 wherein a 2-stilbenyl-1,2,3-triazole of the formula

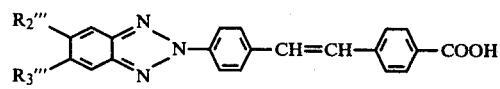

is used.

11. A process according to claim 9 wherein a 2-stilbenyl-1,2,2-triazole of the formula

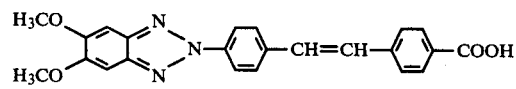

is used.

12. A process according to claim 9 wherein a 2-stilbenyl-1,2,3-triazole of the formula

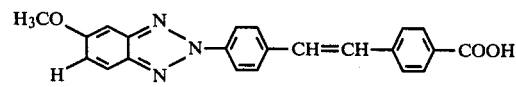

is used.

* * * * *